(12) United States Patent
Shefer et al.

(10) Patent No.: US 6,589,562 B1
(45) Date of Patent: *Jul. 8, 2003

(54) MULTICOMPONENT BIODEGRADABLE BIOADHESIVE CONTROLLED RELEASE SYSTEM FOR ORAL CARE PRODUCTS

(75) Inventors: Adi Shefer, East Brunswick, NJ (US); Shmuel David Shefer, East Brunswick, NJ (US)

(73) Assignee: Salvona L.L.C., Dayton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/696,148

(22) Filed: Oct. 25, 2000

(51) Int. Cl.$^7$ .............................. A61K 9/14; A61K 9/16; A61K 9/50; A61F 2/00; A61F 13/00

(52) U.S. Cl. ..................... 424/490; 424/426; 424/435; 424/484; 424/485; 424/486; 424/489; 424/501; 424/502

(58) Field of Search .......................... 424/49, 52, 426, 424/439, 489, 490, 435, 484, 485, 486, 501, 502

(56) References Cited

U.S. PATENT DOCUMENTS

| | | | |
|---|---|---|---|
| 4,780,320 A | | 10/1988 | Baker |
| 5,055,303 A | | 10/1991 | Riley, Jr. |
| 5,061,106 A | * | 10/1991 | Kent .......................... 401/268 |
| 5,077,051 A | * | 12/1991 | Gallopo et al. ............. 424/435 |
| 5,403,578 A | * | 4/1995 | Gordon ....................... 424/53 |
| 5,625,004 A | | 4/1997 | Harrison et al. |
| 5,702,687 A | * | 12/1997 | Miskewitz ................... 424/52 |
| 5,939,080 A | | 8/1999 | Michael et al. |
| 5,955,502 A | | 9/1999 | Hansen et al. |
| 5,976,506 A | * | 11/1999 | Vernon ........................ 424/49 |
| 5,989,535 A | | 11/1999 | Nayak |
| 5,989,583 A | | 11/1999 | Amselem |
| 5,993,846 A | | 11/1999 | Friedman et al. |
| 5,998,431 A | | 12/1999 | Tseng et al. |
| 6,007,795 A | * | 12/1999 | Masterman et al. .......... 424/49 |
| 6,042,792 A | | 3/2000 | Shefer et al. |

FOREIGN PATENT DOCUMENTS

| | | |
|---|---|---|
| EP | 0 908 174 A2 | 4/1999 |
| WO | WO 93/00076 | 1/1993 |

* cited by examiner

*Primary Examiner*—Thurman K. Page
*Assistant Examiner*—S. Tran
(74) *Attorney, Agent, or Firm*—Mathews, Collins, Shepherd & McKay, P.A.

(57) ABSTRACT

The present invention relates to a controlled release system useful for site'specific delivery of biologically active ingredients or sensory markers, over an extended period of time, targeting biological surfaces comprising the oral cavity and mucous membranes of various tissues, as well as the controlled release of the biological active ingredients or sensory markers. The controlled release system of the present invention is a nano-particle encapsulated in a moisture sensitive micro-particle. The nano-particle having an average particle diameter of from about 0.01 microns to about 10 microns, which comprises a biodegradable solid hydrophobic core and a bioadhesive/mucoadhesive positively charged surface. The invention also relates to the use of the nano-particles of the present invention in consumer oral hygiene products, such as toothpaste or mouthwash, for treatment and prevention of periodontal disease. The nano-particles of the present invention are particularly effective for targeted controlled delivery of biological active ingredients into the periodontal pocket. The present invention also provides synchronizing the release of the biologically active ingredient with that of the sensory markers to convey to the consumer the product performance and signal that a new application of the product is needed.

27 Claims, 1 Drawing Sheet

MULTICOMPONENT BIODEGRADABLE BIOADHESIVE CONTROLLED RELEASE SYSTEM FOR ORAL CARE PRODUCTS

BACKGROUND OF THE INVENTION

1. Field of the Invention

This invention relates to bioadhesive controlled release systems useful for targeted delivery of biologically active ingredients, such as anti-septic or antibacterial materials, anti-inflammatory, and other active ingredients that interdict the attachment, propagation, growth and or colonization of bacteria on teeth or sensory markers such as flavors and cooling agents to biological surfaces comprising the oral cavity and mucous membranes of various tissues, as well as the release of these active ingredients or sensory markers over an extended period of time. More specifically, the invention pertains to biodegradable bioadhesive and mucoadhesive nano-particles encapsulated within a moisture sensitive microparticle for oral hygiene products such as toothpaste or mouthwash, that sustain the release of biological active ingredients for treatment and prevention of periodontal disease or the release of sensory markers that provide extended sensation of freshness and malodor coverage over an extended period of time.

2. Description of the Related Art

Decreasing the amount of bacteria in the mouth has long been the target of personnel working in the health care field. The oral care industry and health research communities have searched for many years for a way to interdict the attachment, propagation, growth and or colonization of bacteria on teeth since adherence of bacteria is the start of a pernicious chain of events leading to the formation of home care-resistant plaque, calculus, and ultimately, tooth-loss. As the life expectancy of people in developing countries has increased, dental care plays a larger role in overall health, and developing countries are becoming more aware of the importance of oral hygiene. Considering the prevalence of periodontal disease, there is an ongoing need for improved, more effective agents, as well as technology, that inhibit plaque growth to maximize the reduction of oral decay and disease associated with plaque formation.

Periodontal disease, also known as pyorrhea or gum disease, is a major cause of tooth loss in adults. Tooth loss from periodontal disease is a significant problem beginning at about age 35, or even younger. It is estimated that about 4 out of 5 persons already have gingivitis and 4 out of 10 have periodontitis. 75% of the US population suffers from periodontal disease and this epidemic costs billions of dollars a year. The greatest single cause of periodontal disease is poor hygiene, indicated by the appearance of bacterial plaque and tartar (calcified plaque). It is believed that plaque and tartar are more sinister when they occur below the gum line than when they occur at or above the gum line.

Several approaches to fight periodontal disease have been described in patents and in literature. One of the approaches uses liposomes to deliver biologically active ingredients to the oral cavity. Several reports of liposome suspensions containing bioadhesive polymers have been published. The problems with using liposomes and structured vesicles as delivery devices are that these types of systems are unstable and can only be used for encapsulation of certain types of materials. Stability has become the major problem limiting the use of liposomes for controlled delivery, both in terms of shelf life and after administration. Liposomes and vesicles do not remain intact or available in vivo for more than a few hours to a couple of days.

U.S. Pat. No. 5,989,535 discloses a polymeric controlled release composition specifically targeted to the organs that contain mucus membranes at the interface. The invention discloses a polymeric bioadhesive composition that delivers drugs to the target tissue in a sustained manner. The bioadhesive polymer is a water dispersible high molecular weight crosslinked polyacrylic acid copolymer with free carboxylic acid groups further crosslinked with a combination mono, di and polyvalent metal ions, cationic polymers and surfactants. The type of metal ion and the concentration can be adjusted to get the desired adhesive properties along with several physical properties that are important to the formulation of dosage forms.

U.S. Pat. No. 5,993,846 discloses methods for making oil-in-water emulsions having mucoadhesive properties. The emulsion includes a hydrophobic core, a surfactant, and a mucoadhesive polymer which is a polymer or copolymer of acrylic acid or methacrylic acid, a poly (methyl vinyl ether/maleic anhydride) copolymer, pectin, alginic acid, hyaluronic acid, chitosan, gum tragacanth, karaya gum or carboxymethylcellulose surrounding the hydrophobic core. Emulsions of this invention contain a bioadhesive macromolecule or polymer in an amount sufficient to confer bioadhesive properties. The bioadhesive macromolecule enhances the delivery of biologically active agents on or through the target surface. The bioadhesive macromolecule may be selected from acidic nonnaturally occurring polymers, preferably having at least one acidic group per four repeating or monomeric subunit moieties, such as poly(acrylic)- and/or poly(methacrylic) acid (e.g., Carbopol, Carbomer), poly(methylvinyl ether/maleic anhydride) copolymer, and their mixtures and copolymers; acidic synthetically modified natural polymers, such as carboxymethylcellulose (CMC); neutral synthetically modified natural polymers, such as (hydroxypropyl)methylcellulose; basic amine-bearing polymers such as chitosan; acidic polymers obtainable from natural sources, such as alginic acid, hyaluronic acid, pectin, gum tragacanth, and karaya gum; and neutral nonnaturally occurring polymers, such as polyvinylalcohol; or their mixtures. The ionizable polymers may be present as free acids, bases, or salts, usually in a final concentration of 0.01–0.5% (w/vol).

U.S. Pat. No. 5,077,051 discloses bioadhesive microcapsules which permit the sustained release of active agents such as therapeutic or cosmetic agents into, the oral cavity. The bioadhesive microcapsules capable of sustained release comprise of xanthan gum, locust bean gum, a bulking agent and an active agent. The microcapsules are spray-dried or coated with wax and are prepared by a process which comprises spray drying a solution comprising the active agent xanthan gum, locust bean gum and a bulking agent.

U.S. Pat. No. 5,403,578 discloses a stable tooth and gum dentifrice that includes a non-aqueous carrier containing urea, hydrated silica, fluoride, sodium bicarbonate, pyrophosphate, and a peroxide, one or more of the ingredients being microencapsulated and which in use functions as an aid in preventing periodontal disease by reducing incidents of plaque as well as controlling tartar formation, and also as an aid in preventing dental caries and oral odors; and the method of compounding such improved tooth and gum paste. The microencapsulated peroxide may consist of a blend of 75% by weight of calcium peroxide and 25% by weight of calcium hydroxide. The peroxide constituent is provided with an ethylcellulose coating that consists of 6.5% by weight of the finished product.

U.S. Pat. No. 6,007,795 discloses a method for inhibiting bacteria in the mouth of a patient which includes placing a particle containing a degradable material and an anti-microbial agent in the mouth of the patient. In general, the invention features a method for inhibiting bacteria in the mouth of a patient that includes placing a particle containing a degradable material and an anti-microbial agent into the mouth of a patient. The saliva in the mouth causes the degradable material in the particle to degrade, resulting in the release of the anti-microbial agent in a controlled manner over time. The exterior of the particle is water-stable allowing the particles to be incorporated into, for example, aqueous rinses or pastes without the water in the rinse or paste causing the degradable material to degrade prematurely, prior to use.

WO 93/00076 discloses a drug delivery system of microparticles having a spherical core composed of a biopolymer, preferably a protein such as albumin or gelatin, which typically has been crosslinked or denatured to maintain its structural coherency. The spherical core is suggested to be combined with a bioadhesive polymer.

U.S. Pat. No. 5,061,106, discloses capsules or microspheres in the tuft holes in which the bristles of a toothbrush are mounted. The capsules or microspheres include a disinfectant or medicant that is released during use. A dye may also be included in the structures. The dye also is released over time to enable the user to become aware of when the contents of the capsules are depleted.

U.S. Pat. No. 5,939,080 discloses oral compositions and methods for reducing plaque in a human or lower animal subject comprising applying to the teeth of the subject an oral composition comprising one or more hydrophobic solvents having one or more characteristics selected from the group consisting of a hydrogen bonding parameter of less than about 7.0 and a water solubility of less than about 10%; one or more non-polymeric surfactants wherein the weight ratio of hydrophobic solvent to non-polymeric surfactant is from about 30:1 to about 1:2; and one or more aqueous carriers; wherein the oral composition is in the form of a toothpaste or mouthrinse, is non-ingestible, and has a pH of from about 5.0 to about 9.5. Preferred hydrophobic solvents include triacetin, diethyl malate, diethyl succinate, benzyl alcohol, phenylethyl alcohol, ethyl acetate, diethyl sebacate, ethyl acetoacetate, diethyl tartrate, butyl lactate, and ethyl lactate. The most preferred hydrophobic solvents are triacetin, diethyl malate, diethyl succinate, benzyl alcohol, phenylethyl alcohol, and butyl lactate. Suitable non-polymeric surfactants are those which are reasonably stable and foam throughout a wide pH range. The non-polymeric surfactants may be anionic, select nonionic, amphoteric, zwitterionic, cationic, or mixtures thereof.

U.S. Pat. No. 5,976,506 discloses oral care products such as toothpastes with an improved sensorially-perceivable cleaning benefit. This is achieved by the inclusion in the oral care products of agglomerates, substantially free from organic and/or inorganic binding agents, whereby the agglomerates are made of at least two, chemically and/or physically different particulate materials of specified particle sizes. The inclusion of materials having a therapeutic benefit on the teeth or gums in the agglomerates such as zinc citrate provides for a further benefit in that this material is slowly released from the agglomerates, thus providing for a delivery of this material over a longer period. Upon use, the gritty-feeling agglomerates will break-down into smaller particles, thus giving the consumer the feeling of initial cleaning and subsequent polishing.

U.S. Pat. No. 5,955,502 describes the use of fatty acid esters as bioadhesive substances. The fatty acid esters of the invention have molecular weights below about 1000 dalton and the fatty acid component of the fatty acid ester is a saturated or unsaturated fatty acid having a total number of carbon atoms of from $C_8$ to $C_{22}$. Bioadhesive properties where observed for fatty acid esters of glyceryl monooleate, glyceryl monolinoleate or glyceryl monolinolenate. A method is described for administering active or protective substance to undamaged or damaged skin or mucosa of an animal such as a human by combining the active or protective substance with a bioadhesive fatty acid ester. The created particles have no charge on their surface.

U.S. Pat. No. 4,780,320 discloses a controlled release drug delivery system for placement in the periodontal pocket. The microparticles are prepared by the solvent evaporation process and are between 10 and 500 microns in size. The matrix of the microparticles consist of cellulose acetate, ethylcellulose, polystyrene, polysulfone, polycarbonate and lacticglycolic acid copolymers.

U.S. Pat. No. 4,989,583 discloses dry solid lipid compositions for the oral delivery of lipophilic substances enhanced their oral bioavailability. The dry solid lipid is composed of a lipophilic substance, a lipid, and one or more phospholipids.

In conventional controlled release systems no precautions are made in order to localize the delivery system after administration and, furthermore, the contact time in vivo between the controlled release system and a particular site is often so short that no advantages are to be expected with respect to, e.g., modifying tissue permeability.

It is desirable to provide a controlled release system formed of biodegradable bioadhesive/mucoadhesive nanoparticles encapsulated within a moisture-sensitive microparticle that provides targeted delivery and extended release of biological active ingredients and/or sensory markers for oral and hygiene products, wherein the release rate of the biological active ingredient is synchronized with that of a sensory marker.

SUMMARY OF THE INVENTION

The present invention relates to a multicomponent controlled release delivery system comprising biodegradable bioadhesive nano-particles encapsulated in a moisture sensitive micro-particle to provide site-specific delivery of biologically active ingredients or sensory markers for targeting and adhering to biological surfaces comprising the oral cavity and mucous membranes of various tissues. The multi-component controlled release system of the present invention sustains the release of the biological active ingredients or sensory markers over an extended period of time. The present invention also provides a method for making a multi-component release system comprising biodegradable nano-particles having bioadhesive properties encapsulated within a moisture sensitive micro-particle.

The nano-particles of the present invention comprise a cationic surfactant that is entrapped and fixed to the particle surface. The bioadhesive properties of the nano-particles are attributed to the positively charged surfactant entrapped on the particle surface as the hydrophobic ends of the surfactants are embedded in the solid core and the hydrophilic ends are exposed on the surface of the nano-particles. The cationic surface active materials useful in the present invention, are believed to attach to tooth surfaces via a complexing interaction between the cationic portion of the material and the proteinaceous portion of the tooth and thus predispose or condition the surface of the tooth so that the nano-particles will then adhere to the surface.

Preferably, the nano-particles are formed of a solid inner core. The combination of a solid inner core with a cationic exterior provides several advantages of the nano-particles as compared with conventional microspheres, liposheres, and microparticles, including high dispersibility in an aqueous medium, and a release rate for the entrapped substance that is controlled by the hydrophobic material barrier properties as well as the barrier properties of the hydrophilic layer of cationic surfactant. There are also many advantages over other dispersion-based delivery systems. Nano-particles have increased stability as compared to emulsion-based delivery systems, including vesicles and liposomes, and are more effectively dispersed than most suspension based systems. The substance to be delivered does not have to be soluble in the vehicle since it can be dispersed in the solid matrix. The nano-particles of the present invention also have a lower risk of reaction of substance to be delivered with the vehicle than in emulsion systems because the vehicle is a solid inert material. The altering of either, or both, the inner solid core or the outer surfactant layer can manipulate the release rate of the substance from the nano-particles.

The multi-component release system of the present invention can generally be incorporated into any suitable oral hygiene product known in the art. Exemplary oral hygiene products include gels, chewing gums, toothpaste, and mouthwash. The oral hygiene product can be appropriately selected depending upon the physical location that the nano-particles are to be delivered to, as well as the intended use of the nano-particles. The above-described exemplary oral hygiene products are preferred in accordance with the present invention, since they permit effective delivery of the bioadhesive nano-particles encapsulated in a moisture sensitive micro-particle into the oral cavity. The toothpaste or mouthwash, containing the biodegradable bioadhesive nano-particles is useful for treatment and prevention of periodontal disease and that provide a flavor "burst" as well as extended sensation of freshness and malodor coverage in the mouth over an extended period of time. Another aspect of the present invention is to provide oral hygiene products, such as toothpaste or mouthwash, containing the biodegradable bioadhesive nano-particles where the release rate of the biological active ingredients is synchronized with that of a sensory marker to convey to the consumer the product performance.

In another aspect of the present invention the oral hygiene products containing the nano-particles of the invention are useful for targeted delivery of biological active ingredients into the periodontal pocket. The controlled release system of the present invention takes advantage of the anatomical features of the gingiva and adjacent tissues, as a site that can hold the nano-particles for a prolonged period of time. It has also been found that the junctional epithelium, which joins the tooth surface and the keratinised gingival oral epithelium, is a thin, non-keratinised tissue, lacking membrane-coating granules which make this region highly permeable to the nano-particles of the present invention.

Accordingly, the invention provides a biodegradable bioadhesive nano-particle encapsulated within a moisture-sensitive micro-particle for oral or hygiene compositions of matter characterized by one or more of the following:

(i) site-specific delivery of biologically active ingredients or sensory markers, targeting and adhering to biological surfaces comprising the oral cavity and mucous membranes of various tissues;

(ii) controlled, continuous release of effective levels of biological active ingredients or sensory markers over an extended period of time;

(iii) extended sensation of freshness or malodor coverage in the mouth over an extended period of time; and (iv) the release rate of the biological active ingredients is synchronized with that of a sensory marker.

The invention also provides a method for producing the bioadhesive nano-particles encapsulated within a moisture sensitive micro-particle, which comprises the steps of:

heating a hydrophobic core material to a temperature above the material melting-point;

dissolving or dispersing the active ingredients or the sensory marker into the melt;

dissolving or dispersing a water sensitive material, positively charged surfactant, the biological active agents or sensory marker in the aqueous phase;

heating the composition to a temperature above the melting point of the formed mixture composed of the hydrophobic materials;

mixing the hot melt with the aqueous solution to form a suspension;

high shear homogenization of the suspension at a temperature above the melting temperature until a homogeneous fine suspension is obtained; and rapidly cooling the suspension to ambient temperature to form a dispersion; and spray drying the dispersion to form a dry powder composition.

The introduction of active agents such as anti-septic or antibacterial materials, anti-inflammatory, and other such active agents targeting biological surfaces, comprising the oral cavity and mucous membranes of various tissues, into the oral cavity by sustained release has the advantage of reducing the number of times an active agent must be administered, and further provides a uniform distribution of the active agent over an extended period of time. Nano-particles, due to their small size, have been found to penetrate regions that may be inaccessible from other delivery systems, such as the periodontal pocket areas below the gum line. The use of biodegradable nano-particles as intra-pocket delivery systems also has the advantage that there is no need to remove them from the treated area.

Bioadhesive substances, also denoted mucoadhesive substances, are generally known to be materials that are capable of being bound to a biological membrane and retained on that membrane for an extended period of time. Compared with conventional controlled release systems, bioadhesive controlled release systems have the following advantages:

i) a bioadhesive controlled release system localizes a biological active ingredient in a particular region, thereby improving and enhancing the bioavailability for active ingredients which may have poor bioavailability by themselves, ii) a bioadhesive controlled release system leads to a relatively strong interaction between a bioadhesive substance and a mucosa, such an interaction contributes to an increasing contact time between the controlled release system and the tissue in question and permits localization of the active released from the controlled release system to a specific site, iii) a bioadhesive controlled release system prolongs delivery of biological active ingredients in almost any non-parenteral route, iv) a bioadhesive controlled release system can be localized on a specific site with the purpose of local therapy, v) a bioadhesive controlled release system can be targeted to specific diseased tissues, and vi) a bioadhesive controlled release system is useful when conventional approaches are unsuitable, such as for certain biological active ingredients which are not adequately absorbed.

BRIEF DESCRIPTION OF THE DRAWING

For a better understanding of the present invention, reference may be made to the accompanying drawing.

DETAILED DESCRIPTION

Figure 1:
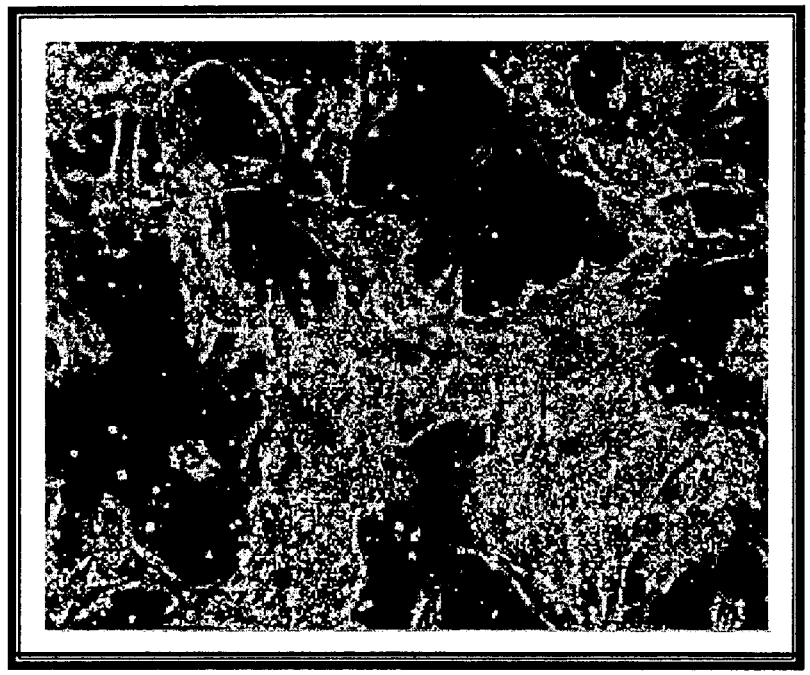
FIG. 1 is an image showing bioadhesion of nano-particles generated by example I of the detailed description.

The present invention relates to a controlled release system of biologically active ingredients or sensory markers to the oral cavity and mucous membranes of various tissues. Preferably, the controlled release system comprises a biologically active agent or sensory marker incorporated into substantially solid nano-particles encapsulated in moisture sensitive micro-particles. The nano-particles have a hydrophobic core and a positively charged surface. The positively charged surface is formed by a cationic surfactant that is entrapped and fixed to the particle's surface.

I. Moisture Sensitive Micro Particles

The micro particles of the present invention comprise water sensitive materials for encapsulating bioadhesive solid hydrophobic nano particles. The microparticles can also include biologically active agents and sensory markers. Suitable water sensitive materials include a starch derivatives, natural gums, polyvinyl alcohol, proteins, hydrocolloid or mixture of thereof.

The multi-component water sensitive micro particles of the present invention preferably have a size of from about 0.5 micron to about 300 microns, more preferably from about 1 micron to about 200 microns, most preferably from about 2 microns to about 50 microns. The present invention preferably has minimal active agents on the surface of the particles, preferably less than 1%.

II. Nano-Particles

The nano-particle comprises a substantially solid core. Preferably, the solid core is formed of an inert hydrophobic material. The nano-particles have a particle diameter between about 0.01 microns and about 10 microns that comprise a positively charged cation surfactant that is embedded on the surface of the particles adhere to biological surfaces of the oral cavity and mucous membranes of various tissues and have the ability to sustain the release of biologically active ingredients or sensory markers.

Preferably, the nano-particles of the present invention have an average diameter of about 0.01 to about 10 microns. The core of the solid nano-particle contains a biologically active material, such as a drug, anti-septic material antibacterial material, anti-inflammatory, and other such active ingredients that interdict the attachment, propagation, growth or colonization of bacteria on teeth. The core of the nano-particle can also include vitamins, zinc, calcium, and the like. The core of the nano-particle can also contain a sensory markers, such as cooling agents and flavors. The biologically active materials or the sensory markers can be either hydrophilic or hydrophobic.

The nano particles also comprise a bioadhesive, positively charged surfactant. Preferably, the surfactant is cetylpyridinium chloride. The nano-particle can also contain antioxidants, preservatives, microbicides, buffers, osmoticants, cryoprotectants, and other known pharmaceutically useful additives or solutes.

The nano-particles sustain the release rate of biologically active materials or sensory markers for an extended period of time. For example, the nano-particles sustain the release of biologically active materials or sensory markers for a period between about ten minutes and about three months. Preferably the release rate of the nano-particles for the biologically active materials can be from about 30 minutes to about three months and the release rate for the sensory markers can be from about 10 minutes to about six hours.

The use of nano particles which provide varying rates of diffusion are contemplated. For example, nano particles may diffuse at any rates of the following:

(i) at steady-state or zero-order release ratein which there is a substantially continuous release per unit of time;

(ii) a first-order release rate in which the rate of release declines towrds zero with time; and (iii) a delayed release in which the initial rate is slow, but then increases with time.

III. Bioadhesive/Mucoadhesive Positively Charged Surfactant

The term "a bioadhesive substance" is broadly defined as a material that is capable of being bound to a biological membrane and retained on that membrane for an extended period of time. The term "bioadhesion" relates to the attachment of a material to a biological substrate such as a biological membrane. The term "mucoadhesive" is defined as a material in which an adhesive bonding is established between a material and the mucosa/mucus/mucin of a biological membrane. The term "mucoadhesive substance" is in accordance with the generally accepted terminology and is used synonymously with the term "a bioadhesive substance". The temperature referred to as the "melting temperature" is defined as the temperature at which the solid core material becomes liquid, and the cationic surfactant coating is entrapped and fixed to the particle surface.

A cationic surfactant is incorporated on an outer surface of the nano-particle to form a bioadhesive nanoparticle. The surfactant is believed to be entrapped and fixed to the particle surface and forms a coating at the interface surrounding the particle core. The interface surrounding the core is hydrophobic. The cationic surface active materials are believed to attach to tooth surfaces via a complexing interaction between the cationic portion of the material and the proteinaceous portion of the tooth for predisposing the surface of the tooth to allow the nano-particles to adhere to the surface of the tooth. The cationic surfactant also stabilizes the outer surface of the hydrophobic core component of the nano-particles, thereby promoting a more uniform particle size.

Surface active materials that are capable of strong bonding to the negatively charged and hydrophilic surfaces of human teeth are preferable for use as cationic charged surfactants. Suitable surface active materials include straight-chain alkylammonium compounds, cyclic alkylammonium compounds, petroleum derived cationics, and polymeric cationic materials. Cetylpyridinium chloride was found to exhibit strong bioadhesive properties on biological surfaces, and is a preferred surface active material. The surfactant is present in a proportion of about 0.01% to about 5%, preferably about 0.05% to about 2%, by weight of the nano-particles.

IIIa) Straight-chain Alkylammonium Compounds

Straight-chain alkylammonium compounds are cationic surface active materials in which one or more hydrophobic alkyl groups are linked to a cationic nitrogen atom. The linkage can also be more complex as, for example, in R—CO—NHCH$_2$ CH$_2$ CH$_2$ N(CH$_3$)$_2$. Alternatively, the cationic surface active material can contain more than one cationic nitrogen atom such as the class of compounds of R—NHCH$_2$CH$_2$ CH$_2$ NH$_2$ and derivatives thereof. Representative examples of suitable compounds for the cationic surfactant include: cetyl trimethylammonium chloride (CTAB), hexadecyltrimethylammonium bromide (HDTAB), stearyl dimethylbenzylammonium chloride, lauryl dimethylbenzylammonium chloride, cetyl dimethylethylammonium halide, cetyl dimethylbenzylammonium halide, cetyl trimethylammonium halide, dodecyl ethyldimethylammonium halide, lauryl trimethylammonium halide, coconut alkyltrimethylammonium halide, and N,N—C$_{8-20}$-dialkyldimethylammonium halide. Other suitable compounds for the cationic surfactant include bis(hydrogenated tallow alkyl) dimethylammonium chloride which is known to adsorb onto the surface with hydrophobic groups oriented away from it, 2-hydroxydodecyl-2-hydroxyethyl dimethyl ammonium chloride and N-octadecyl-N,N',N'-tris-(2-hydroxyethyl)-1,3-diaminopropane dihydrofluoride.

IIIb) Cyclic Alkylammonium Compounds

Surface-active quaternary ammonium compounds in which the nitrogen atom carrying the cationic charge is part of a heterocyclic ring can be used as the cationic surfactant. Examples of suitable compounds are laurylpyridinium chloride, bromide laurylpyridinium, tetradecylpyridinium bromide, and cetylpyridinium halide where the halide is selected from chloride, bromide or fluoride.

IIIc) Petroleum Derived Cationics

Petroleum-based raw materials which can be used as the cationic surfactant include olefins, paraffins, and aromatic hydrocarbons. Suitable compounds include at least one aliphatic carbon chain containing six or more carbon atoms attached to nitrogen. For example, amine salts, diamines, amidoamines, alkoxylated amines, and their respective quaternary salts are useful as the cationic surfactant. Preferred petroleum derived compounds of this type include tallow or coco alkyl substituted 1,3-propylene diamines, such as are manufactured by Witco under the trade names of "Adogen" and "Emcol" and similar diamines manufactured by Akzo under the trade name "Duomeen" and polyethenoxy derivatives manufactured under the trade names of "Ethomeen" and "Ethoduomeens".

IIId) Polymeric Amines

Polymeric amines which can be used as the cationic surfactant comprise a class of polymers containing ionic groups along the backbone chain and exhibit properties of both electrolytes and polymers. These materials contain nitrogen, of primary, secondary, tertiary or quaternary functionality in their backbone and may have weight average molecular weights as low as about 100 or higher than about 100,000. Suitable polymeric amines useful as a cationic surfactant include polydimeryl polyamine available from General Mills Chemical Co., polyamide, polyacrylamides, polydiallyldimethylammonium chloride, polyhexamethylene biguanide compounds, and also other biguanides, for example those disclosed in U.S. Pat. Nos. 2,684,924, 2,990,425, 3,183,230, 3,468,898, 4,022,834, 4,053,636 and 4,198,425, herein incorporated by reference into this application, 1,5-dimethyl-1,5-diazaundecamethylene polymethobromide, such as "Polybrene" manufactured by Aldrich, polyvinylpyrrolidone and their derivatives, polypeptides, poly(allylamine) hydrochloride, polyoxyethylenated amines, and polyethyleneimine, such as "Polymin" manufactured by BASF.

Suitable polymeric materials for the cationic surfactant also include surface active cationic polymers prepared by converting a fraction of the amino groups to their acyl derivatives. For example, the polyethyleneimine is first condensed with less than the stoichiometric quantity of acid halides thus alkylating some of the amino groups and the remaining amino groups are then condensed with hydrogen halides such as hydrogen chloride or, preferably, hydrogen fluoride. The surface activity of these compounds varies with the number of amino groups which are acylated and with the chain length of the acylating group RCO. The condensation reaction can be performed with stearic or oleic acid chlorides in the presence of a solvent containing metal fluoride, preferably silver fluoride, in such a manner that metal chloride formed in the reaction precipitates from the solvent.

Also suitable, for the purpose of this invention, are cationic derivatives of polysaccharides such as dextran, starch or cellulose, for example, diethylaminoethyl cellulose. Examples of applicable copolymers based on acrylamide and a cationic monomer are available from Hercules Inc. under the trade name RETEN including RETEN 220, or from National Adhesives under the trade name FLOC AID including FLOC AID 305. Other useful acrylamide-based polyelectrolytes are available from Allied Colloids under the trade name PERCOL. Further examples of suitable materials are cationic guar derivatives such as those sold under the trade name JAGUAR by Celanese-Hall.

Another further preferred group of compounds suitable for the cationic surfactant which comprises a class of water-insoluble polymers, having nitrogen atoms in their molecules, include quaternary polymers of quaternary ammonium type, betaine-type, pyridylpyridinium type or vinylpyridinium-type. Examples of this group of compounds are: poly(vinyl-benzylmethyllaurylammonium chloride), poly(vinyl-benzylstearylbetaine), poly(vinyl-benzyllaurylpyridylpyridinium chloride), poly(vinyl-benzylcetylammonylhexyl ether) and quaternized polyoxyethyleneated long chain amines having the formula RN(CH$_3$)[(C$_2$ H$_4$ O)$_x$H]$_2$(+)A(-), where A(-) is generally chloride or fluoride, x is a number from 1 to 20, and R is C$_{8-22}$-alkyl.

A strongly ionic bond is produced upon reacting the above described cationic surfactants with dental surfaces.

IV. Core Hydrophobic Barrier Materials

The nanoparticle hydrophobic core is preferably formed of a biodegradable hydrophobic materials having barrier properties. The term "degradable material", as used herein, means a material which degrades within three months when placed in the mouth of a typical patient. The materials degrade as a result of exposure to one or more enzymes that commonly are found in the mouth. These enzymes include lipases, proteases, and glucosidases.

Suitable, nontoxic, pharmaceutical solid core materials are inert hydrophobic biocompatible materials with a melting range between about 50 degrees and about 120 degrees C. Examples are natural, regenerated, or synthetic waxes including: animal waxes, such as beeswax; lanolin and shellac wax; vegetable waxes such as carnauba, candelilla, sugar cane, rice bran, and bayberry wax; mineral waxes such as petroleum waxes including paraffin and microcrystalline wax; cholesterol; fatty acid esters such as ethyl stearate, isopropyl myristate, and isopropyl palmitate; high molecular weight fatty alcohols such as cetostearyl alcohol, cetyl alcohol, stearyl alcohol, and oleyl alcohol; solid hydrogenated castor and vegetable oils; hard paraffins; hard fats; biodegradable polymers such as polycaprolactone, polyamides, polyanhydrides, polycarbonates, polyorthoesters, polylactic acids, and copolymers of lactic acid and glycolic acid; cellulose derivatives and mixtures thereof. Other hydrophobic compounds which may be used in the present invention include triglycerides, preferably of food grade purity or better, which may be produced by synthesis or by isolation from natural sources. Natural sources may include animal fat or vegetable oil, such as, soy oil, a source of long chain triglycerides (LCT). Other suitable triglycerides are composed predominantly of medium length fatty acids (C10–C 18), denoted medium chain triglycerides (MCT). The fatty acid moieties of such triglycerides can be unsaturated, monounsaturated or polyunsaturated. Mixtures of triglycerides having various fatty acid moieties are also useful for the present invention. The core can comprise a single hydrophobic compound or a mixture of hydrophobic compounds. Hydrophobic materials are known to those skilled in the art and are commercially available, as described in the list of suitable carrier materials in Martindale, The Extra Pharmacopoeia, The Pharmaceutical Press, 28th Edition pp 1063–1072 (1982). Considerations in the selection of the core material include good barrier properties to the active ingredients and sensory markers, low toxicity and irritancy, biocompatibility, stability, and high loading capacity for the active ingredients of interest.

V. Biologically Active Agents

It has been found that streptococcus mutans, and streptococcus sobrinus, are the bacteria shown to be major sources of bacterial plaque colonies and their sequelae. The types of materials that inhibit or defeat the attachment or propagation, growth or colonization of bacteria on dental surfaces are various cetyl amines, nitroparaffin derivatives, duomeens, ethoxylated duomeens, and other quaternary ammonium compounds. Especially useful is 5-Amino-1,3-bis(2-ethylhexyl)-5-methylhexahydropyrimidine, such are available from Angus Chemical Co. by the trade name hexetidine. Descriptions of other suitable drugs within these therapeutic classifications illustratively can be found in Goodman and Gilman's Pharmacological Basis of Therapeutics, eighth edition (1990).

Biologically active ingredient in the present invention can also include an effective amount of an anticalculus agent. An effective amount, as used herein, is any amount of an anticalculus agent sufficient to be effective in reducing calcium phosphate mineral deposition related to calculus formation. Suitable anticalculus agents include pyrophosphate salts such as the dialkali metal pyrophosphate salts, tetra alkali metal pyrophosphate salts, and mixtures thereof. Disodium dihydrogen pyrophosphate ($Na_2 H_2 P_2 O_7$), tetrasodium pyrophosphate ($Na_4P_2O_7$), and tetrapotassium pyrophosphate ($K_4 P_2 O_7$) in their unhydrated as well as hydrated forms are the preferred species. In compositions of the present invention, the pyrophosphate salt can be present in one of three ways: substantially dissolved, substantially undissolved, or a mixture of dissolved and undissolved pyrophosphate.

Compositions comprising substantially dissolved pyrophosphate refer to compositions where at least one pyrophosphate ion source is present in an amount sufficient to provide at least about 1.0% free pyrophosphate ions. The amount of free pyrophosphate ions can be from about 1% to about 15%, preferably from about 1.5% to about 10%, and most preferably from about 2% to about 6%, by weight of the composition. Free pyrophosphate ions can be present in a variety of protonated states depending on a the pH of the composition.

Compositions comprising substantially undissolved pyrophosphate as the anticalculus agent refer to compositions containing no more than about 20% of the total pyrophosphate salt dissolved in the composition, preferably less than about 10% of the total pyrophosphate dissolved in the composition. Tetrasodium pyrophosphate can be in the anhydrous salt form or the decahydrate form or as any other species stable in solid form in the dentifrice compositions. The pyrophosphate salt is in its solid particle form, which can be its crystalline or amorphous state, with the particle size of the salt preferably being small enough to be aesthetically acceptable and readily soluble during use. The amount of pyrophosphate salt useful in making these compositions is any tartar control effective amount. The effective amount can be about 1.5% to about 15%, preferably from about 2% to about 10%, and most preferably from about 2.5% to about 8%, by weight of the composition. Some or all of the tetrasodium pyrophosphate can be undissolved in the product and present as tetrasodium pyrophosphate particles. Pyrophosphate ions in different protonated states such as, $HP_2O_7^{-3}$ can be present depending upon the pH of the composition and if a portion of the tetrasodium pyrophosphate is dissolved.

A mixture of dissolved and undissolved pyrophosphate salts can comprise a mixture of any of the above described pyrophosphate salts. Suitable examples of pyrophosphate salts useful for practice of the present invention are also described in more detail in Kirk & Othmer, Encyclopedia of Chemical Technology, Fourth Edition, Volume 18, Wiley-Interscience Publishers (1996), Incorporated herein by reference in its entirety, including all references incorporated into Kirk & Othmer.

Other anticalculus agents which can be used instead of the pyrophosphate salt of or in combination with the pyrophosphate salt include such materials known to be effective in reducing calcium phosphate mineral deposition related to calculus formation. Suitable anticalculus agents include synthetic anionic polymers including: polyacrylates and copolymers of maleic anhydride or acid and methyl vinyl ether available from ISP Technologies Inc. as Gantrez, such as described, for example, in U.S. Pat. No. 4,627,977, the disclosure of which is incorporated herein by reference in its entirety; polyamino propane sulfonic acid (AMPS); zinc citrate trihydrate; diphosphonates, such as EHDP and AHP; polypeptides, such as polyaspartic and polyglutamic acids, and mixtures thereof. Polyphosphates can also be used as an anticalculus agent. Polyphosphate is generally understood to consist of two or more phosphate molecules arranged primarily in a linear configuration, although some cyclic derivatives may be present. Inorganic polyphosphate salts include tetrapolyphosphate and hexametaphosphate. Polyphosphates larger than tetrapolyphosphate usually occur as amorphous glassy materials. Examples of polyphosphates are manufactured by FMC Corporation as Sodaphos, Hexaphos, and Glass H and are described in more detail in Kirk & Othmer, Encyclopedia of Chemical Technology, Fourth Edition, Volume 18, Wiley-Interscience Publishers (1996), incorporated herein by reference in its entirety, including all references incorporated into Kirk & Othmer.

Other biologically active ingredients useful to counter bacterial attachment and plaque formation are antimicrobial. Preferred anti-microbial agents include, triclosan, phenolic compounds which can be monomeric or polymeric, synthetic or natural; nature-derived anti-microbials such as sanguinarine; cetylpyridinium salts; benzalkonium salts; benzethonium salts; domiphen salts; bisbiguanides, such as chlorhexidene; bisbiguanide salts; phosphonium salts; ammonium salts; peroxides and other oxidants; zinc salts; and antibiotics such as penicillin, vancomycin, kanamycin, erythromycin, niddamycin, spiramycin, tetracycline, minocycline, and metronidazole. Particularly preferred antimicrobial agents include triclosan, chlorhexidene or an acceptable salt of chlorhexidene. When chlorhexidene is selected as the anti-microbial agent, the controlled delivery process of the invention results in a reduction of undesirable side effects, such as staining of the teeth and tongue. It has been found that, when the particles of the present invention are composed of a degradable material and an anti-microbial agent, substantially nothing remains of the particles in the mouth or body once the degradable material degrades and all of the anti-microbial agent is released. A particularly preferred anti-microbial agents are an anti-bacterial compound which contains two biguanide moieties, such as triclosan and chlorhexidene, each attached in the para position to a separate chlorophenyl group, and joined by a hexane linkage (see, for example, Rose et al., J. Chem Soc., p. 4422 (1956) and U.S. Pat. No. 2,684,924). Pharmaceutically acceptable salts of chlorhexidene, such as chlorhexidene gluconate, chlorhexidene diacetate, chlorhexidene dihydrochloride, chlorhexidene dihydrofluoride, and chlorhexidene dihydrobromide can also be used in the present invention. Chlorhexidene and its associated salts are commercially available. The gluconate salt can be purchased, for example, as a 20.5 percent w/w aqueous solution from Pliva Pharmaceutical of Zagreb, Yugoslavia, and from ICI Ltd. of England. Chlorhexidene gluconate as a freeze-dried solid is available from Pliva Pharmaceutical.

Suitable drugs which can be administered in the drug delivery system of the present invention include: antibacterial agents such as thimerosal, chloramine, boric acid, phenol, iodoform, chlorhexidine and other oral antiseptics; beta-lactam antibiotics, for example cefoxitin, n-formamidoyl thienamycin and other thienamycin derivatives, tetracyclines, chloramphenicol, neomycin, gramicidin, kanamycin, amikacin, sismicin and tobrarnycin; anti-inflammatory steroids such as cortisone, hydrocortisone, beta-methasone, dexamethasone, fluocortolone, prednisolone, triamcinolone and the like; non-steroidal anti-inflammatory drugs including flurbiprofen, ibuprofen, indomethacin, piroxicam, naproxen, antipyrine, phenylbutazone and aspirin; plaque dissolving substances, for example lysozyme chloride or amylase; and local anaesthetics such as lidocaine, procaine, benzocaine, xylocaine and the like. It will be appreciated that other conventional anti-bacterial agents can be incorporated into the present invention. The biologically active ingredient can also be one or more antibiotics, such as penicillin, polymyxin B, vancomycin, kanamycin, erythromycin, niddamycin, metronidazole, spiramycin and tetracycline.

The compositions of the present invention can further comprise a source of calcium ions selected from the group of calcium salts, calcium sulfate, calcium phosphate, calcium acetate, calcium formate, calcium lactate, calcium nitrate and mixtures thereof.

The compositions of the present invention can further comprise a source of zinc. For example, the source of zinc can be selected from the group of zinc acetate, zinc ammonium sulfate, zinc benzoate, zinc bromide, zinc borate, zinc citrate, zinc chloride, zinc gluconate, zinc glycerophosphate, zinc hydroxide, zinc iodide, zinc oxide, zinc propionate, zinc D-lactate, zinc DL-lactate, zinc pyrophosphate, zinc sulfate, zinc nitrate, and zinc tartrate.

The compositions of the present invention can further comprise a source of fluoride. Suitable sourcing of fluoride include sodium fluoride, potassium fluoride, tin fluoride, zinc fluoride, organic fluorides such as long-chained aminofluorides, for example oleylaminofluoride, cetyl aminofluoride or ethanolaminohydrofluoride, fluorosilicates, for example, potassium hexafluorosilicate or sodium hexafluorosilicate, fluorophosphates such as ammonium, sodium, potassium, magnesium or calcium fluorophosphate and fluorozirconates, for example sodium, potassium or tin fluorozirconate.

Cetylpyridinium chloride is biologically active ingredient that posses both anti-bacterial activity and bioadhesive/mucoadhesive surface activity. Other materials having these properties which can be used in the present invention include are described in: U.S. Pat. Nos. 2,984,639, 3,325, 402, 3,431,208, and 3,703,583, and British Patents No. 1,319,396 hereby incorporated by reference in their entirety into this application.

VI. Sensory Marker

The present invention provides for synchronization of the release of the sensory markers such as flavors and cooling agents with that of the active antibacterial agent. The release of the sensory markers can be used to convey to the consumer the product performance, provide long lasting freshness, and signal to the consumer that a new application of the product is needed. It has been found that many consumers would prefer for the flavor present in oral care product to remain in the mouth for an extended period of time to convey a lasting impression of freshness.

It will be understood herein that a flavoring composition is one capable of imparting a definite flavor to a tasteless or bland foodstuff. A flavor-enhancing composition is understood to be one capable of reinforcing one or more flavor notes of a natural or other material which is deficient in flavor. A flavor-enhancing composition would be useful for improving the flavor of, for example, a meat product, the flavor of which was diminished or undesirably altered by processing. Flavoring compositions can include flavoring ingredients, carriers, vehicles and the like to form compositions suitable for imparting a flavor to, enhancing the flavor in, or altering the flavor of a product composition.

Flavoring compositions used in the present invention can be used to enhance existing flavors in or to provide the entire flavor impression to a foodstuff. Suitable flavoring compositions can include organic acids, including fatty, saturated, unsaturated and amino acids; alcohols, including primary and secondary alcohols, esters, carbonyl compounds including aldehydes and ketones, lactones, cyclic organic materials including benzene derivatives, alicyclics, heterocyclics such as furans, pyridines, pyrazines and the like; sulfur-containing materials including thiols, sulfides, disulfides and the like, proteins, lipids, carbohydrates; and flavor potentiators such as monosodium glutamate, guanylates, inosinates, and natural flavoring materials such as vanillin, and the like. It will be appreciated that the types and amounts of materials selected from the foregoing groups of materials will depend upon the precise organoleptic character desired in the finished product and, especially in the case of flavoring compositions used to enhance other flavors, will vary according to the foodstuff to which the flavor and aroma are to be imparted. Inorganic materials such as sodium chloride and freshness preservers such as butylated hydroxyanisole, butylated hydroxytoluene and propyl gallate can be added for their adjuvant preservative effects on the flavoring composition or on the final food composition itself. Typical examples of usable flavor compounds useful for practice of the present invention are described in S. Arctander, Perfume and Flavor Chemicals, Montclair, N.J., (USA) (1969).

VII. Micro Particle Matrix

The water-sensitive materials for forming micro particles of the present invention comprise starch derivatives, natural gums, polyvinyl alcohol, proteins, hydrocolloids, polycarboxylate compounds and mixtures thereof. In the preferred embodiment water sensitive materials are natural gums, polyvinyl alcohol, proteins, polycarboxylate compounds, and mixtures thereof.

A suitable starch derivative is a water dispersible, modified starch, such as Capsul®, N-Lok®, Hi-Cap™ 100 or Hi-Cap™ 200 commercially available from the National Starch and Chemical Company of Bridgewater, N.J., and Pure-Cote™ commercially available from the Grain Processing Corporation of Muscatine, Iowa. In the preferred embodiment a suitable natural gum is a gum arabic, commercially available from TIC Gums Inc. Belcamp, Midland. Suitable hydrocolloids are xanthan, maltodextrin, galactomanan or tragacanth, preferably maltodextrins such as Maltrin™ M100, and Maltrin™ M150, commercially available from the Grain Processing Corporation of Muscatine, Iowa.

The polyvinyl alcohol useful in the practice of our invention is partially and fully hydrolyzed polyvinyl acetate, termed "polyvinyl alcohol" with polyvinyl acetate as hydrolyzed to an extent, also termed degree of hydrolysis, of from about 75% up to about 99%. Such materials are prepared by means of any of Examples I–XIV of U.S. Pat. No. 5,051,222 issued on Sep. 24, 1991, the specification for which is incorporated by reference herein. Polyvinyl alcohol useful for practice of the invention is Mowiol® 3–83, having a molecular weight of about 14,000 Da and degree of hydrolysis of about 83%, Mowiol® 3–98, a fully hydrolyzed (98%) polyvinyl alcohol having a molecular weight of 16,000 Da and commercially available from Gehring-Montgomery, Inc. of Warminster Pa. Other suitable polyvinyl alcohols are: AIRVOL® 205, having a molecular weight of about 15,000–27,000 Da and degree of hydrolysis of about 88%, and VINEX® 1025, having molecular weight of 15,000–27,000 Da degree of hydrolysis of about 99% and commercially available from Air Products & Chemicals, Inc. of Allentown, Pa.; ELVANOL® 51–05, having a molecular weight of about 22,000–26,000 Da and degree of hydrolysis of about 89% and commercially available from The Du Pont Company, Polymer Products Department, Wilmington, Del.; ALCOTEX® 78 having a degree of hydrolysis of about 76% to about 79%, ALCOTEX® F88/4 having a degree of hydrolysis of about 86% to about 88% and commercially available from the Harlow Chemical Co. Ltd. of Templefields, Harlow, Essex, England CM20 2BH; GOHSENOL® GL-03 and GOHSENOL® KA-20 commercially available from Nippon Gohsei K. K., The Nippon Synthetic Chemical Industry Co., Ltd., of No. 9-6, Nozaki Cho, Kita-Ku, Osaka, 530 Japan.

In the preferred embodiment, the moisture sensitive matrix is formed of a polyvinyl alcohol material at a level from about 1% to about 80%, preferably from about 1% to about 70% by weight of the matrix material with the balance being the amount by weight of active agent. In the preferred embodiment, the active agent composition is generally present at a level from about 0.01% to about 80% preferably from about 1% to about 50% by weight of the encapsulated active agent with the balance being the polyvinyl alcohol. Optionally other conventional ingredients known in the art such as preservatives, surfactants, can be used in accordance with the teachings of the present invention.

Polyvinyl alcohol is an excellent barrier material to the permeation of the volatile fragrance ingredients, and as a result the controlled release systems of the present invention do not provide perceptible odor in the dry state. Upon wetting by a sufficient amount of aqueous fluid such as a body fluid, the matrix can either dissolve to provide a burst of the active ingredients, or swell and soften the matrix to slowly release the encapsulated active agents over an extended period of time, depending on the composition of the matrix, such as the ratio of polyvinyl alcohol to other matrix materials. The use of moisture activated particles which provide varying rates of diffusion are contemplated. For example, the moisture activated particles may diffuse at any of the rates of the following:

(i) at steady-state or zero-order release rate in which there is a substantially continuous release per unit of time;

(ii) a first-order release rate in which the rate of release declines towards;zero with time; and (iii) a delayed release in which the initial rate is slow, but then increases with time.

Suitable polycarboxylate compounds are 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000 most preferably about 30,000 to about 500,000. These copolymers are commercially available, for example, under the trade designation, as Gantrez, e.g. AN 139 (M.W. 500,000), AN 119 (M.W. 250,000); and preferably S-97 Pharmaceutical Grade (M.W. 70,000.

VIII. Processing Method

The controlled release system of the present invention is prepared by incorporating the selected biologically active materials and sensory marker into the hydrophobic interior of the nano-particles, forming an aqueous mixture comprising, the nano-particles, one or more biologically active materials, sensory marker and water sensitive materials, and spray drying the mixture to form a dry powder composition. The biologically active ingredients and sensory markers can be incorporated into the hydrophobic solid nano particles, into the water sensitive matrix of the micro particle, or in both the nano and the micro particle structure, depending on the mechanism and rate it needs to be released.

A process for producing a multi-component controlled release system comprising the following steps:

heating the hydrophobic core material to a temperature above the material melting point;

dissolving or dispersing the active ingredients or the sensory marker into the melt;

dissolving or dispersing the positively charged surfactant, the biologically active materials or sensory marker, and water sensitive materials in the aqueous phase and heating it to a temperature above the melting point of the melt;

mixing the melt with an aqueous solution to form a suspension;

high shear homogenization of the suspension at a temperature above the melting temperature until a homogeneous fine dispersion is obtained, the suspension having a particle size of from about 1 micron to about 2 microns; and rapidly cooling the suspension to ambient temperature to form a dispersion; and spray drying the mixed dispersion to form a dry powder composition.

Homogenization can be accomplished in any suitable fashion with a variety of mixers known in the art such as simple paddle or ribbon mixers although other mixers, such as ribbon or plow blenders, drum agglomerators, and high shear mixers may be used. Suitable equipment for this process include a model Rannie 100 lab homogenizer available from APV Gaulin Inc. Everett, Mass., a rotor stator high shear mixer available from Silverson Machines, of East Long Meadow, Mass., or Scott Processing Equipment Corp. of Sparta, N.J., and other high sear mixers.

The suspension is spray dried to remove the excess water. Spray drying is well known in the art and been used commercially in many applications, including foods where the core material is a flavoring oil and cosmetics where the core material is a fragrance oil. Cf. Balassa, "Microencapsulation in the Food Industry", CRC Critical Review Journal in Food Technology, July 1971, pp 245–265; Barreto, "Spray Dried Perfumes for Specialties, Soap and Chemical Specialties", December 1966; Maleeny, Spray Dried Perfiunes, Soap and San Chem, January 1958, pp. 135 et seq.; Flinn and Nack, "Advances in Microencapsulation Techniques", Batelle Technical Review, Vo. 16, No. 2, pp. 2–8 (1967); U.S. Pat. Nos. 5,525,367; and 5,417,153 which are incorporated herein as references.

In the preferred embodiment, the active agent is present at a level from about 0.01% to about 60%, preferably from about 1% to about 50% by weight of the micro particle. In the preferred embodiment, the nano particles are generally present in the water sensitive matrix at a level from about 1% to about 80%, preferably from about 1% to about 60% by weight of the matrix material with the balance being the active agents and the water sensitive materials. In the preferred embodiment, the moisture sensitive matrix is generally present at a level from about 1% to about 80%, preferably from about i% to about 60% by weight of the matrix material with the balance being the active agents and the hydrophobic materials.

The method of preparation of nano-particles described herein is characterized by high loading, reproducibility, versatility, and stability. The method is further illustrated in the non-limiting examples.

The use of nano-particles which provide varying rates of diffusion are contemplated. For example, the nano-particles may diffuse at any of the rates of the following:

(i) at steady-state or zero-order release rate in which there is a substantially continuous release per unit of time;

(ii) a first-order release rate in which the rate of release declines towards zero with time; and (iii) a delayed release in which the initial rate is slow, but then increases with time.

The release rate for releasing the active agents from the hydrophobic nano particles is typically slower than the release rate for releasing active agent from the moisture sensitive matrix. The biological active agents or sensory markers can be selected to be incorporated into either the hydrophobic nano particles or the moisture sensitive matrix depending on the desired time for release of the active agents. For example, a predetermined first active agent can be incorporated in the moisture sensitive matrix to be released upon contact and a predetermined second active agent can be incorporated in the hydrophobic nano particles for release over an extended period of time during or after the first agent has been released. For example, the moisture sensitive matrix formed in accordance with the present invention can release a first active agent, such as a sensory marker, upon contact with moisture to provide a "burst" with continued release of the first active agent up to about 6 hours and nano particles formed in accordance with the present invention can release a second active agent, such as a biological active agent, depending on the release rate from an initial time such as within thirty minutes up to a period of three months.

IX. Bioadhesion Measurements

The oral cavity is lined by non-keratinizd, stratified, squamous epithelial cells. This type of epithelial cells also lines other soft tissue surfaces that include esophagus, vagina and cervix. A HeLa cell line that has been used to determine the bioadhesive/mucoadhesive properties of the nano-particles of the present invention is an epithelial-like cell line, originally derived from a carcinoma of the cervix. HeLa cells are cultured in Minimal Essential Medium (Eagles) with 10% fetal bovine serum. To test the adherence of nano-particles to the cell surface, HeLa cells are being plated at a density of $2\times10^5$ cells per dish (35 mm) in 2 ml medium. Three dishes are seeded for each data point. On the following day, the particles are being dispersed in 1 ml medium. The medium in which the cells are cultured is aspirated and replaced immediately with the nano-particles-containing medium. The particles are left to adhere to the cells by gravity for time periods such as 5 minutes, 15 minutes, and 30 minutes. At each time point the medium is aspirated, and the cells surface are gently rinsed twice with 2 ml medium, simulating rinsing the mouth following brush. Cells are imaged immediately using an Olympus IX-70 inverted fluorescent microscope and Princeton Instruments Micromax cooled CCD camera. The images are saved and stored and analyzed using the IPLab Scientific Imaging Software (Scanalytics, Inc, VA) to determine the number of particles adherent to the cells per field. Images from three random fields are collected from each dish. Each experiment generates a total of nine data points, for each time point. The nine data points are averaged. Each experiment is repeated at least 3 times. Results obtained from three or more independent experiments are averaged and expressed as a mean±standard deviation (SD). The data are subjected to statistical analysis using the StatView program using Student's t-test method to determine whether the difference among groups is statistically significant. Results are accepted as significant when $p<0.05$.

The ability of the nano-particles of the present invention described below to adhere to HeLa cultured cells is shown in FIG. 1. FIG. 1 shows specific adhestion of nanoparticles to HeLa cells. FIG. 1 shows bioadhesion of the nanoparticles described in example I.

X. Oral Hvyiene Products

The biodegradable bioadhesive nano-particles provided by the present invention can generally be incorporated into any suitable conventional oral hygiene product. Exemplary delivery systems include gels, chewing gums, toothpaste, and mouthwash. The toothpaste can include other conventional components such as an abrasive such as, silica or alumina, having a particle size of between about 5 microns and about 50 microns, a thickener such as, colloidal silica having a particle size of between about 0.1 microns and about 1 micron, and neat flavor oil. The oral hygiene product can be appropriately selected depending upon the physical location for delivery of the nano-particles and the intended use of the nano-particles. The above-described exemplary delivery systems are preferred in accordance with the present invention, since they permit effective delivery of the bioadhesive nano-particles into the oral cavity.

The invention is illustrated by the following, non-limiting, examples, in which the abbreviations have the meanings commonly used in the art. The following examples illustrate embodiments of this invention. All parts, percentages and proportions referred to herein and in the appended claims are by weight, unless otherwise indicated.

It is understood that the above-described embodiments are illustrative of only a few of the many possible specific embodiments which can represent applications of the principles of the invention. Numerous and varied other arrangements can be readily derived in accordance with these principles by those skilled in the art without departing from the spirit and scope of the invention.

EXAMPLE I

Preparation of Multi-component Release System with Cetylpyridinium Chloride (CPC)

The following procedure is used for the preparation of a multi component controlled release system comprising menthol as sensory marker and cetylpyridinium chloride (CPC) as both the biologically active ingredient and bioadhesive/mucoadhesive surfactant. The solid hydrophobic nano particles are composed of candelilla wax from Strahl & Pitsch Inc. of West Babylon, N.Y.

120 grams of candelilla wax is placed in an oven at 80 degrees C. and allowed to melt. 600 grams of deionized water are placed into 1 Gallon vessel, fitted with an all-purpose silicon rubber heater (Cole-Palmer Instrument Company). 196 grams of polyvinyl alcohol, Mowiol® 3–83, having a molecular weight of about 14,000 Da and degree of hydrolysis of about 83%, commercially available from Gehring-Montgomery, Inc. of Warminster, Pa. and 4 grams of CPC are added to the water and the aqueous solution is heated to 90 degrees C. while mixing it with a propeller mixer. The candelilla wax melt is removed from the oven and 80 grams of menthol are mixed into the wax by hand with a glass rod. The menthol/wax mixture is poured into the aqueous solution and the dispersion is homogenized at 20,000 psi using a Rannie 100 lab homogenizer available from APV Gaulin Inc. The dispersion is cooled to ambient temperature by passing it through a tube-in-tube heat exchanger (Model 00413, Exergy Inc. Hanson Mass.) to form a suspension. The resulting suspension is spray dried with a Bowen Lab Model Drier (at Spray-Tek of Middlesex, N.J.) utilizing 250 c.f.m of air with an inlet temperature of 380° F., and outlet temperature of 225° F. and a wheel speed of 45,000 r.p.m to produce a free flowing, dry powder, consisting of 20% menthol encapsulated in the solid hydrophobic nano particles and 1% CPC in the water sensitive matrix of the micro particles.

The shape and size of the nano-particles was verified by examining the samples under a scanning electron microscope (SEM). SEM studies showed that the nano-particles of Example I were spherical in nature with an average particle size of approximately 1 micron. The microcapsules of Example I were subjected to in vitro bioadhesion measurements, utilizing the technique previously described. Measurements of the adhesion of particles to cells were carried out on the nano-particles of Example I, along with the appropriate controls, using cultured human epithelial HeLa cells as a model system as described previously. The nano-particles of Example II were observed to exhibit excellent bioadhesive properties the cultured cells HeLa cells.

EXAMPLE II

Preparation of Multi-component Controlled Release System with Menthol and Cetylpyridinium Chloride (CPC)

The following procedure is used for the preparation of a multi component controlled release system comprising menthol as sensory marker zinc citrate, and cetylpyridinium chloride (CPC) as both the biologically active ingredient, and bioadhesive/mucoadhesive surfactant. The solid hydrophobic nano particles are composed of carnauba wax from Strahl & Pitsch Inc. of West Babylon, N.Y.

120 grams of carnauba wax is placed in an oven at 80 degrees C. and allowed to melt. 600 grams of deionized water are placed into 1 Gallon vessel, fitted with an all-purpose silicon rubber heater (Cole-Palmer Instrument Company). 176 grams of polyvinyl alcohol, Mowiol® 3–83, having a molecular weight of about 14,000 Da and degree of hydrolysis of about 83%, commercially available from Gehring-Montgomery, Inc. of Warminster, Pa., and 4 grams of CPC are added to the water and the aqueous solution is heated to 90 degrees C. while mixing it with a propeller mixer. The carnauba wax melt is removed from the oven and 80 grams of menthol and 20 grams of zinc citrate are mixed into the wax by hand with a glass rod. The wax mixture is poured into the aqueous solution and the dispersion is homogenized at 20,000 psi using a Rannie 100 lab homogenizer available from APV Gaulin Inc. The dispersion is cooled to ambient temperature by passing it through a tube-in-tube heat exchanger (Model 00413, Exergy Inc. Hanson Mass.) to form a suspension. The resulting suspension is spray dried with a Bowen Lab Model Drier (at Spray-Tek of Middlesex, N.J.) utilizing 250 c.f.m of air with an inlet temperature of 380° F., and outlet temperature of 225° F. and a wheel speed of 45,000 r.p.m to produce a free flowing, dry powder, consisting of 20% menthol and 5% zinc citrate encapsulated in the solid hydrophobic nano particles and 1% CPC in the water sensitive matrix of the micro particles.

The shape and size of the nano-particles was verified by examining the samples under a scanning electron microscope (SEM). SEM studies showed that the nano-particles of Example II were spherical in nature with an average particle size of approximately 0.1 microns. The microcapsules of Example II were subjected to in vitro bioadhesion measurements, utilizing the technique previously described. Measurements of the adhesion of particles to cells were carried out on the nano-particles of Example II, along with the appropriate controls, using cultured human epithelial HeLa cells as a model system as described previously. The nano-particles of Example III were observed to exhibit excellent bioadhesive properties the cultured cells HeLa cells.

EXAMPLE III

Preparation of Multi-component Controlled Release System Sensory Markers and Biologically Active Agents The following procedure is used for the preparation of a multi component controlled release system comprising raspberry and double mint flavors (Noville Inc.) as sensory markers zinc citrate, and cetylpyridinium chloride (CPC) as both the biologically active ingredient, and bioadhesive/mucoadhesive surfactant. The solid hydrophobic nano particles are composed of carnauba wax from Strahl & Pitsch Inc. of West Babylon, N.Y.

120 grams of carnauba wax/is placed in an oven at 80 degrees C. and allowed to melt. 600 grams of deionized water are placed into 1 Gallon vessel, fitted with an all-purpose silicon rubber heater (Cole-Palmer Instrument Company). 136 grams of polyvinyl alcohol Mowiol® 3–83, having a molecular weight of about 14,000 Da and degree of hydrolysis of about 83%, commercially available from Gehring-Montgomery, Inc. of Warminster, Pa., 40 gram of double mint flavor, and 4 grams of CPC are added to the water and the aqueous solution is heated to 90 degrees C. while mixing it with a propeller mixer. The carnauba wax melt is removed from the oven and 80 grams of raspberry flavor and 20 grams of zinc citrate are mixed into the wax by hand with a glass rod. The wax mixture is poured into the aqueous solution and the dispersion is homogenized at 20,000 psi using a Rannie 100 lab homogenizer available from APV Gaulin Inc. The dispersion is cooled to ambient temperature by passing it through a tube-in-tube heat exchanger (Model 00413, Exergy Inc. Hanson Mass.) to form a suspension. The resulting suspension is spray dried with a Bowen Lab Model Drier (at Spray-Tek of Middlesex, N.J.) utilizing 250 c.f.m of air with an inlet temperature of 380° F., and outlet temperature of 225° F. and a wheel speed of 45,000 r.p.m to produce a free flowing, dry powder, consisting of 10% double mint flavor, 20% raspberry flavor, and 5% zinc citrate encapsulated in the solid hydrophobic nano particles and 1% CPC in the water sensitive matrix of the micro particles.

The microcapsules of Example III were subjected to in vitro bioadhesion measurements, utilizing the technique previously described. Measurements of the adhesion of particles to cells were carried out on the nano-particles of Example III, along with the appropriate controls, using cultured human epithelial HeLa cells as a model system as described previously. The nano-particles of Example III were observed to exhibit excellent bioadhesive properties the cultured cells HeLa cells.

The nano-particles produced in Examples I to III, exhibit excellent bioadhesive properties, permit the sustained release of the sensory marker over extended period of time, when used in oral hygiene preparation in accordance with the use of U.S. Pat. No. 5,882,630, issued on Mar. 16, 1999, entitled "Dentifrices Composition", incorporated by reference herein.

EXAMPLE IV

Use of Toothpaste 10 grams of the suspension of Examples I to III is admixed with 90 grams of a toothpaste composition, as described in U.S. Pat. No. 5,882,630, issued on Mar. 16, 1999, entitled "Dentifrices Composition", incorporated by reference herein and containing:

| INGREDIENT | % w/w |
| --- | --- |
| CARBOPOL 974P | 1.00 |
| THICKENING SILICA | 6.50 |

-continued

| INGREDIENT | % w/w |
| --- | --- |
| ABRASIVE SILICA | 14.00 |
| SODIUM FLUORIDE | 0.23 |
| TITANIUM DIOXIDE | 1.00 |
| ADINOL CT 95 | 2.00 |
| SACCHARIN | 0.33 |
| POLYETHYLENE GLYCOL(400) | 17.50 |
| GLYCERIN | qs |

The toothpaste comprising the nano-particles is applied to the teeth by brushing the teeth with 1 gram of the toothpaste comprising the nano-particles and rinsing the teeth with 50 ml. of water two times.

Flavor perception in the mouth following the application of the product consisting of the nano-particles vs. the same product consisting of an equivalent amount of neat flavor, was evaluated organoleptically. A panel test is conducted to determine which product provides the strongest perception of flavor (using a scale of 0–10), after 10 minutes, 1 hour, and 3 hours following application of the product

| | Flavor Intensity (a scale of 1–10) | | |
| --- | --- | --- | --- |
| | 10 minutes | 1 Hour | 3 Hours |
| Toothpaste consisting neat menthol | 3 | 1 | 1 |
| Toothpaste consisting sample of Example I | 6 | 5 | 3 |
| Toothpaste consisting sample of Example II | 5 | 4 | 3 |

The toothpaste containing the multi component controlled release system provided a higher intensity of menthol for an extended period of time, compared to the sample containing the neat menthol. It was readily apparent that the toothpaste containing the inventive multi component system has superior characteristics and provided longer lasting menthol perception.

Brushing the teeth with the toothpaste comprising the multi component system of Example III provided a change in flavor character upon brushing the teeth and provided a long lasting sensation (2 hours) of the raspberry flavor.

What is claimed is:

1. A multi-component moisture activated controlled release delivery system for delivery to biological surfaces comprising an oral cavity or mucous membranes of various tissues, said system comprising:

a plurality of solid nano-particles having a core formed of a biodegradable hydrophobic material selected from the group consisting of natural waxes, synthetic waxes, fatty acid esters, fatty alcohols, solid hydrogenated plant oils, biodegradable natural polymers and synthetic polymers, each of said solid nano-particles comprising a core and an effective amount of a first active agent contained therein and a bioadhesive positively charged surfactant surrounding said core, wherein said positively charged surfactant is selected from the group consisting of straight-chain alkylammonium compounds, cyclic alkylammonium compounds, petroleum derived cationics, and polymeric cationic materials, said plurality of nano-particles being encapsulated in a moisture sensitive microparticle, said microparticle is formed of a moisture sensitive material, wherein said microparticle dissolves upon contact with said moisture to provide a burst of said nanoparticles or said microparticle swells or softens to slowly release said nanoparticles and said nanoparticles release said active agent continuously thereafter for an extended period of time.

2. The system of claim 1 wherein said hydrophobic material has a melting point between 50 degrees C. and 120 degrees C.

3. The system of claim 1 wherein said hydrophobic material comprises candelilla wax.

4. The system of claim 1 wherein said moisture sensitive matrix material is selected from the group consisting of a starch derivative, natural gum, polyvinyl alcohol, protein, hydrocolloid, polycarboxylate, and mixtures thereof.

5. The system of claim 4 wherein said hydrocolloid is selected from the group consisting of xanthan, maltodextrin, galactomanan, and tragacanth.

6. The system of claim 4 wherein said natural gum is gum arabic.

7. The system of claim 4 wherein said polyvinyl alcohol has a degree of hydrolysis from about 75% to about 99%.

8. A multi-component moisture activated controlled release delivery system for delivery to biological surfaces comprising an oral cavity or mucous membranes of various tissues, said system comprising:

a plurality of solid nano-particles having a core formed of a biodegradable hydrophobic material, each of said solid nano-particles comprising a core and an effective amount of a first active agent contained therein and a bioadhesive positively charged surfactant surrounding said core, said plurality of nano-particles being encapsulated in a moisture sensitive microparticle, said microparticle is formed of a moisture sensitive material, wherein said first active agent is a biologically active agent selected from the group consisting of anti-septic materials, antibacterial materials, anti-inflammatory materials and active ingredients that interdict the attachment, propagation, growth and or colonization of bacteria on teeth.

9. The system of claim 8 wherein the first active agent is said antibacterial material selected from the group consisting of thimerosal, chloramine, boric acid, phenol, iodoform, chlorhexidine, oral antiseptic, beta-lactam antibiotic, cefoxitin, n-formamidoyl thienamycin, thienamycin derivatives, tetracycline, chloramphenicol, neomycin, gramicidin, kanamycin, amikacin, sismicin and tobramycin.

10. The system of claim 1 wherein said first active agent is a sensory marker selected from the group consisting of a flavor, sweetener and cooling agent.

11. A multi-component moisture activated controlled release delivery system for delivery to biological surfaces comprising an oral cavity or mucous membranes of various tissues, said system comprising:

a plurality of solid nano-particles having a core formed of a biodegradable hydrophobic material, each of said solid nano-particles comprising a core and an effective amount of a first active agent contained therein and a bioadhesive positively charged surfactant surrounding said core, said plurality of nano-particles being encapsulated in a moisture sensitive microparticle, said microparticle is formed of a moisture sensitive material, wherein said microparticle dissolves upon contact with said moisture to provide a burst of said nanoparticles or said microparticle swells or softens to slowly release said nanoparticles and said nanoparticles release said active agent continuously thereafter for an extended period of time, wherein said first active agent is a biological active agent and further comprising a second active agent, said second active agent is a sensory marker.

12. The system of claim 11 wherein a release rate of said first active agent is synchronized with a release rate of said second active agent.

13. The system of claim 1 wherein said positively charged surfactant is cetylpyridinium chloride.

14. The system of claim 1 wherein said bioadhesive is a mucoadhesive.

15. The system of claim 1 wherein said system remains active for a period between about ten minutes and about 3 months.

16. The system of claim 1 wherein said nano-particles adhere to said oral cavity or mucous membranes of various tissues.

17. The system of claim 1 wherein said nano-particles provide one or more of the following site specific adhesion: settling around the gumline; settling subgingivally; penetrating into periodontal pocket; adhering to soft tissue; and becoming immobilized over an extended period of time.

18. By The system of claim 1 wherein said nano-particles have an average particle diameter between about 0.01 microns and about 10 microns.

19. The system of claim 1 wherein said nano-particles further comprise a preservative.

20. The system of claim 1 wherein said positively charged surfactant includes hydrophobic ends and hydrophilic ends said hydrophobic ends of said positively charged surfactant are embedded in said core and said hydrophilic ends of said positively charged surfactant are exposed on a surface of said core.

21. A multi-component moisture activated controlled release delivery system for delivery to biological surfaces comprising an oral cavity or mucous membranes of various tissues, said system comprising:

a plurality of solid nano-particles having a core formed of a biodegradable hydrophobic material, each of said solid nano-particles comprising a core and an effective amount of a first active agent contained therein and a bioadhesive positively charged surfactant surrounding said core, said plurality of nano-particles being encapsulated in a moisture sensitive microparticle, said microparticle is formed of a moisture sensitive material, wherein said first active agent is a biologically active agent selected from the group consisting of anti-septic materials, antibacterial materials, anti-inflammatory materials and active ingredients that interdict the attachment, propagation, growth and or colonization of bacteria on teeth further comprising a second active agent in said moisture sensitive matrix wherein said matrix releases said second active agent upon contact with said moisture and continuously thereafter for an extended period of time.

22. The system of claim 21 wherein said composition releases an effective amount of said second active agent to provide a burst of said active agent.

23. The system of claim 22 wherein after said burst of said second active agent, said second active agent is continuously released for an extended period of time.

24. The system of claim 21 wherein said second active agent is a biologically active agent.

25. The system of claim 21 wherein said second active agent is a sensory marker.

26. A method for producing a system for delivery to biological surfaces comprising an oral cavity or mucous membranes of various tissues, said system comprising:

a plurality of solid nano-particles having a core formed of a biodegradable hydrophobic material, each of said solid nano-particles comprising a core and an effective amount of a first active agent contained therein and a bioadhesive positively charged surfactant surrounding said core, said plurality of nano-particles being encapsulated in a moisture sensitive microparticle, said microparticle is formed of a moisture sensitive material comprising the steps of:

(i) heating a core material forming said core to a temperature above said core material melting point to form a melt;

(ii) dispersing said first active agent or sensory marker into said melt;

(iii) dispersing said positively charged surfactant said first active agent or sensory marker and a water sensitive material in the aqueous phase;

(iv) heating the suspension to a temperature above the melting point of the mixture formed in step (ii) to form a hot melt;

(v) mixing said hot melt of step (ii) with the aqueous solution formed in step (iii) to form a suspension;

(vi) high shear homogenization of said suspension at a temperature above the melting temperature of said material mixture formed in step (v) until a homogeneous fine suspension is obtained;

(vii) rapidly cooling said suspension to ambient temperature to form a dispersion; and (viii) spray drying said cooled dispersion to form a dry powder composition.

27. An oral hygiene product comprising the system of claim 1.

* * * * *